(12) United States Patent
Smith et al.

(10) Patent No.: US 7,629,487 B2
(45) Date of Patent: Dec. 8, 2009

(54) ALKALINE EARTH-BASED ALKOXYLATION CATALYSTS

(75) Inventors: George A. Smith, The Woodlands, TX (US); James O'Neill, Houston, TX (US); Lindy R. Coker, legal representative, Houston, TX (US); George Sneed, Spring, TX (US); Christopher J. Whewell, Georgetown, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 163 days.

(21) Appl. No.: 11/661,064

(22) PCT Filed: May 31, 2005

(86) PCT No.: PCT/US2005/019050

§ 371 (c)(1),
(2), (4) Date: Feb. 20, 2008

(87) PCT Pub. No.: WO2006/025898

PCT Pub. Date: Mar. 9, 2006

(65) Prior Publication Data

US 2008/0249330 A1    Oct. 9, 2008

Related U.S. Application Data

(60) Provisional application No. 60/604,656, filed on Aug. 26, 2004.

(51) Int. Cl.
*C07C 69/76* (2006.01)
*B01J 31/00* (2006.01)
*C07C 43/00* (2006.01)

(52) U.S. Cl. .................... 560/55; 560/29; 560/179; 560/126; 502/172; 568/606; 568/618

(58) Field of Classification Search ............... 502/150, 502/170, 172, 340; 560/29, 55, 115, 126, 560/160, 179; 568/606, 618, 622, 678
See application file for complete search history.

(56) References Cited

U.S. PATENT DOCUMENTS 4,375,564 A    3/1983    Edwards (Continued)

FOREIGN PATENT DOCUMENTS

| PL | 166429 B1 | 5/1995 |
|----|-----------|--------|
| WO | WO 0238269 A | 5/2002 |

OTHER PUBLICATIONS

Instytut Clezkiej Syntezy Organicznej, May 31, 1995, PL 166429, (English translation of Abstract) 1 page.*

*Primary Examiner*—Porfirio Nazario-Gonzalez
*Assistant Examiner*—Yate' K Cutliff
(74) *Attorney, Agent, or Firm*—Huntsman Petrochemical LLC

(57) ABSTRACT

Provided herein are catalysts useful in enabling and promoting the insertion of alkylene oxides into ester linkages. The esters employed as a substrate to be alkoxylated include esters of fatty acids, such as methyl esters of $C_{14}$ to $C_{22}$ fatty acids, and mono-, di-, and tri-esters of glycerine, including vegetable oils, animal fats, and plant oils. A catalyst according to the invention includes at least two alkaline earth compounds, which may include any known stable compounds of the alkaline earths, and optionally contains one or more additional materials such as a carboxylic acid or a polyalkylene glycol having a molecular weight between about 100 and 1500 or a $C_1$-$C_{10}$ alkyl-capped polyalkylene glycol having molecular weight between about 100 and 1500, which has been acidified with a strong mineral acid. The preferred alkaline earths employed are salts and compounds of magnesium and calcium.

37 Claims, 1 Drawing Sheet

U.S. PATENT DOCUMENTS

| | | |
|---|---|---|
| 4,453,022 A | 6/1984 | McCain et al. |
| 4,754,075 A | 6/1988 | Knoph et al. |
| 4,775,653 A * | 10/1988 | Leach et al. ............... 502/170 |
| 5,110,991 A | 5/1992 | Champion et al. |
| 5,191,104 A | 3/1993 | King |
| 5,220,046 A | 6/1993 | Leach et al. |
| 5,627,121 A * | 5/1997 | Lin et al. ................... 502/170 |
| 7,119,236 B2 * | 10/2006 | Weerasooriya et al. ...... 568/606 |
| 2005/0240064 A1 * | 10/2005 | Weerasooriya et al. ...... 568/679 |

* cited by examiner

ALKALINE EARTH-BASED ALKOXYLATION CATALYSTS

CROSS-REFERENCES TO RELATED APPLICATIONS

This Application claims priority to U.S. Provisional application Ser. No. 60/604,656 filed Aug. 26, 2004, the entire contents of which are herein incorporated by reference thereto.

TECHNICAL FIELD

This invention relates generally to novel catalysts. More particularly, it relates to catalysts useful in the production of alkoxylated surfactants, such as alkoxylated methyl esters, alkoxylated alcohols, alkoxylated fatty acids, and alkoxylated glyceryl esters, including alkoxylated triglycerides.

BACKGROUND

The supply of detergent-range alcohols ($C_{12}$-$C_{18}$), which are widely employed as hydrophobes in the manufacture of surfactants has become very tight recently, thus causing a rise in their cost. To offset the effects of the supply situation relative to detergent-range alcohols, manufacturers of surfactants may desire to seek out lower-cost hydrophobes. One alternate to the use of detergent range alcohols is methyl esters. However, the alkoxylation of methyl esters is more difficult than the alkoxylation of alcohols, and require a different catalyst system.

SUMMARY OF THE INVENTION

The present invention provides a method for forming a catalyst useful for promoting the alkoxylation of alcohols and/or esters with one or more alkylene oxides, which comprises the steps of: a) combining an alkaline-earth compound (preferably a compound of calcium) with a carboxylic acid to form a first mixture; b) adding a strong mineral acid, such as sulfuric acid, to said first mixture to form a second mixture; and c) mixing the second mixture to a uniform appearance. Additionally, optional materials such as solvents, carriers, fluidizers, etc. may be present at any stage of the process for producing the catalyst. Polyalkylene glycols and polyoxy-alkylated alcohols, including alkyl-end-capped glycol ethers, are preferably, including those sold by Huntsman, LLC of Houston Tex. under the tradename POGOL® MP-116 glycol ether.

Another aspect of the present invention provides a method for forming a catalyst useful for promoting the alkoxylation of carboxylic acids, alcohols, and esters with one or more alkylene oxides, which comprises the steps of: a) combining an alkaline-earth compound (preferably a compound of calcium), with one or more additional materials selected from the group consisting of: a carboxylic acid, a polyalkylene glycol having a molecular weight between about 100 and 1000, an $C_1$-$C_{10}$ alkyl-capped polyalkylene glycol having molecular weight between about 100 and 1000, and mixtures including any of the foregoing, to form a first mixture; b) combining said first mixture with at least one ionic chemical species selected from the group consisting of: sulfuric acid, an organic sulfonic acid, an organic sulfonate, a sulfate, a bisulfate, a sulfite, a bisulfite, any $C_1$-$C_{12}$ carboxylic acid, or any $C_1$-$C_{12}$ carboxylate so as to form a second mixture; and c) mixing said second mixture to a uniform appearance, to provide a finished catalyst.

BRIEF DESCRIPTION OF THE DRAWINGS

In the annexed drawings.

DETAILED DESCRIPTION

Figure 1:
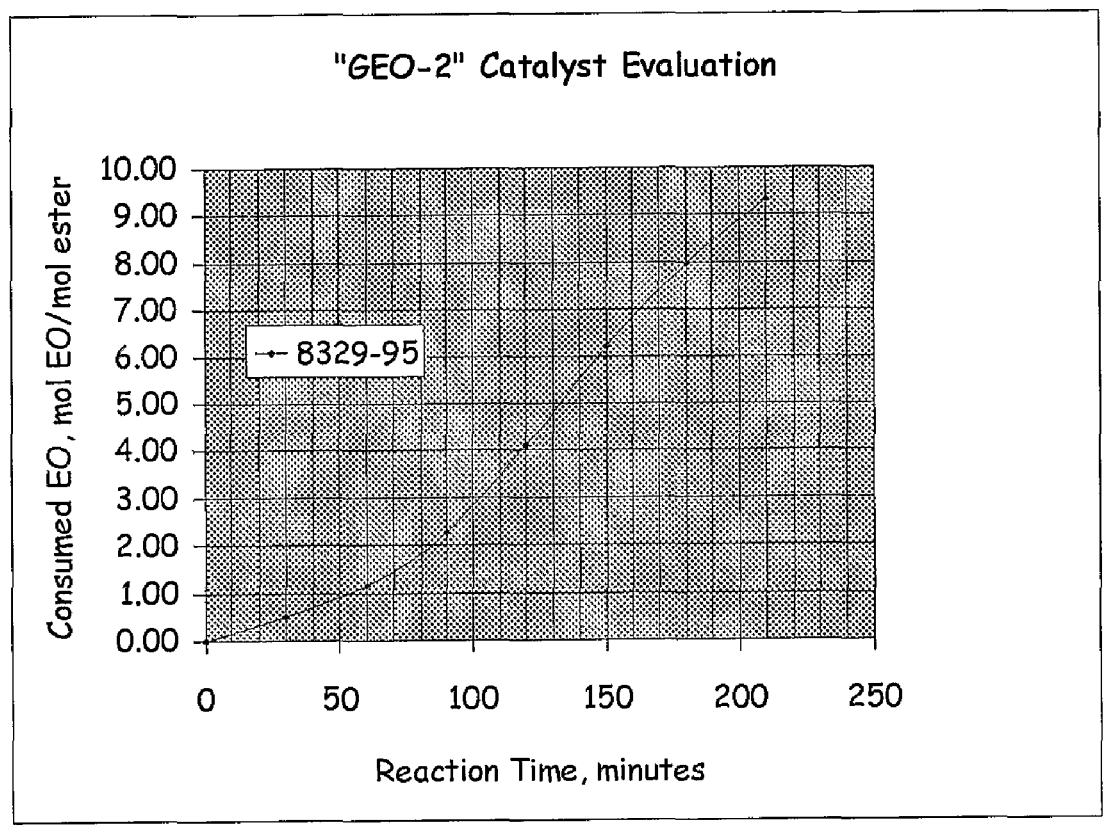
FIG. 1 depicts graphically the consumption of ethylene oxide in a reactor charged with a methyl ester of a fatty acid and a catalyst according to one form of the present invention.

We have found that viable catalysts for the alkoxylation of methyl esters of acids, alcohols, and carboxylic acids results when a mixture comprising one or more carboxylic acids and an ionic alkaline-earth metal salt (preferably a calcium salt), is treated with a strong mineral acid. According to a preferred process of the invention, the mineral acid is concentrated sulfuric acid which contains at least 95% by weight of $H_2SO_4$. A catalyst resulting from the foregoing process according to the invention is generally useful for producing alkoxylated products having a narrow oligomer distribution.

The Alkaline Earth Component

The present invention involves the addition of strong acid to a mixture that comprises an alkaline earth compound. It is preferred, but not necessary, that the alkaline earth compound is an ionic alkaline earth compound having a solubility in water of at least 2 grams per liter at 25° C. Thus, the chlorides, bromides, iodides, nitrates, nitrites, phosphates, phosphites, sulfates, sulfites, carboxylates, alkoxides, fluoborates, fluosilicates, etc. are all suitable salts of alkaline earth metals which can be used in a process of the present invention. Further, the use of mixtures comprising two or more alkaline earth materials which each comprise the foregoing anions in forming a catalyst material is within the scope of the present invention. It is preferred that the alkaline earth metal salt be a calcium salt, and in this regard calcium acetate is especially preferred. In another embodiment, the amount of magnesium present in a mixture from which a catalyst of the present invention is formed is between about 0.1 and 1.0% by weight based on the total amount of calcium compound present—i.e., the alkaline earth compound used is a mixture of calcium acetate and magnesium acetate, which contains between about 0.1% and 1.0% by weight of magnesium, based on the total combined weight of the calcium and magnesium present.

In another embodiment, the alkaline earth component comprises a mixture of alkaline earth compounds, with one of the compounds being a major component and with the other compound being a minor component, wherein the ratio of the alkaline earth atoms present in the major component to number of alkaline earth atoms in the minor component is in the range of between about 9:1 to about 10,000:1. In such an embodiment, it is in one case preferred that a calcium compound comprises the major component and a magnesium compound comprises the minor component. Calcium acetate which contains about 0.5% by weight of magnesium is an especially preferred alkaline earth compound useful as a raw material in the production of a catalyst according to the present invention.

The Acid Component

It is preferred, but not necessary, that the acid component is a strong acid, which is freely dissociated (100% ionized) in water. Such acids are well-known to chemists. Stated alternatively, an acid suitable for use in preparing a catalyst according to the invention should have an acid strength (degree of dissociation, as measured in water) which is at least as strong as the conjugate acid of the anion of the alkaline earth compound raw material used. For example, in the case where a mixture of calcium acetate and magnesium acetate are employed as raw material, the acid used to form a catalyst according to the invention should have an acid dissociation constant that is greater than that for acetic acid.

The Carboxylic Acid Component

A composition from which a catalyst may be prepared according to the invention may contain a carboxylic acid. It is preferable, though not necessary, that the carboxylic acid be a fatty acid. In fact, any carboxylic acid having between about 2 and 25 carbon atoms, whether straight-chain, branched, cyclic, aromatic, aliphatic, alkylaryl. Suitable acids include those which contain a single, two, three, or more carboxylic acid functions per molecule. Additionally, the carboxylic acid component may contain, one, two, or three olefinic bonds (double bonds, a.k.a., "unsaturation"), or may be saturated. An especially preferred acid is oleic acid.

The Ether Component

A catalyst according to the present invention may include an ether component, which is preferably a polyether material, such as a polyalkylene glycol; a polyalkylene glycol having an alkyl group on one or both ends, wherein the alkyl group on the ends may be any $C_1$ to $C_{25}$ hydrocarbyl group; a polyoxyalkylated carboxylic acid; or essentially any polymer (block or random) of a $C_1$ to $C_6$ alkylene oxide which is liquid at room temperature. In one preferred embodiment, the ether component has a molecular weight between about 100 and 1500. In another embodiment, the ether component has a molecular weight between about 100 and 1000. Within this description are included polyalkylene glycols having a molecular weight between about 100 and 1000, and $C_1$-$C_{10}$ alkyl-capped polyalkylene glycols having molecular weight between about 100 and 1000. Any mixtures including any of the foregoing are suitable for use in the present invention.

A catalyst according to one embodiment of the present invention is prepared by adding powdered calcium acetate to oleic acid, and mixing until a uniform dispersion is obtained. A preferred apparatus for rendering the mixture homogeneous is a model L 4RT-A mixer made by Silverson of Waterside, Chesham, Bucks in the United Kingdom. Concentrated sulfuric acid is then added slowly to the mixture, with agitation, and after addition of all of the sulfuric acid, the mixture is again dispersed on the L4RT-A Silverson. Such a process yields a liquid which functions as a catalyst in alkoxylation reactions involving substrates including methyl esters of fatty acids, carboxylic acids, and alcohols.

The following examples shall be construed as being exemplary of the present invention and not delimitive thereof in any way.

EXAMPLE 1

An alkoxylation catalyst was prepared by combining 90 grams of PRIOLENE® 6933 oleic acid and 48 grams calcium acetate monohydrate in a 500 ml beaker. The calcium acetate was dispersed using the above-mentioned Silverson mixer. To this was slowly added 12 grams of concentrated sulfuric acid over a period of about 1 minute, with agitation. The mixture initially turns black which goes to yellow upon mixing. Subsequently, the mixture was dispersed using the Silverson mixture until homogeneous. The reaction mixture was allowed to cool and a further quantity of 50 grams of Priolene added to give a low viscosity dispersion containing 30% active catalyst.

The kinetics of the reaction were obtained by measuring the pressure and the amount of EO (ethylene oxide) added over the course of an alkoxylation of a methyl ester known as EDENOR® MEPK12-18 from COGNIS Corporation. A graph of the reaction profile is depicted in FIG. 1.

Preparation of a Catalyst According to the Invention May be Conducted Using any carboxylic acid having between about 3 and 30 carbon atoms per molecule, including carboxylic acids which are considered as being aliphatic, aromatic, linear, branched, and cyclic, whether saturated or containing 1-3 olefinic linkages by those skilled in the art. However, it is preferred that the carboxylic acid used to prepare a catalyst according to the invention are fatty acids having between about 10 and 20 carbon atoms per molecule. Especially preferred are carboxylic acids having between about 8 and 20 carbon atoms with one or more double bonds in their molecular structure. Thus, the following acids are included, without limitation, within the foregoing description: capric, capryllic, caproic, octanoic, decanoic, docosanoic, erucic, dodecanoic, tetradecanoic, oleic, hexadecanoic, linoleic, linolenic, octadecanoic, and other carboxylic acids.

Although calcium acetate is preferred as a source of calcium ion in providing a catalyst according to the invention, the present invention contemplates utilization of any known stable salt of calcium, including without limitation any one or more of the following anions: halide anions ($F^-$, $Cl^-$, $Br^-$, $I^-$), anions of any carboxylic acid, anions of any mineral acid such as, halic anions, halous anions, perhalic anions, hypohalous anions, nitrate anions, nitrite anions, sulfate anions, sulfite anions, carbonate anions, bicarbonate anions, phenolate anions, etc. However, it is most preferable to employ a calcium salt of a carboxylic acid.

In a process of alkoxylation employing a catalyst according to the present invention, which may exist in the form of a homogeneous paste, or a liquid that is milk-like in appearance, the preferred catalyst currently contains about 30 wt % calcium calculated as the sulfate, and is optimally present at between about 0.1% and about 3% by weight based on final batch weights for alkoxylating alcohol ethoxylates and alkyl esters. In the case of methyl esters, the catalyst is preferably present at about 2% by weight of the batch weight, and in the case of alcohol alkoxylates it is preferably present at about 0.25%.

Typically, the catalyst is added to the initiator (optional) prior to alkylene oxide addition. The preferred temperature range of the alkoxylation is between about 160° C. and 185° C. and the alkoxylation is preferably carried out at about 60 PSIG; however, any temperature and pressure known to those skilled in the art as being suitable for alkoxylations may be employed.

Thus, a reaction that a catalyst as described herein is useful in catalyzing may be depicted as:

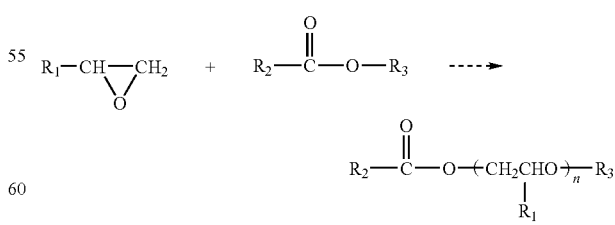

in which $R_1$ is independently selected from the group consisting of: hydrogen and any $C_1$-$C_5$ alkyl group, but is preferably hydrogen or methyl; $R_2$ is independently any $C_6$ to $C_{24}$ hydrocarbyl group and is preferably predominantly $C_{12}$-$C_{18}$, n is any value between about 1 and about 60, and $R_3$ is independently hydrogen or any $C_1$-$C_6$ hydrocarbyl group, preferably methyl or ethyl. (As used in this specification and the appended claims, the word "hydrocarbyl", when referring to a substituent or group is used in its ordinary sense, which is well-known to those skilled in the art. Specifically, it refers to a group having a carbon atom directly attached to the remainder of the molecule and having predominantly hydrocarbon character. Examples of hydrocarbyl substituents or groups include: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy); (3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.) Although the reaction above is written with the R1 group appended to the distal end of the alkoxylate moiety with respect to the carbonyl carbon, the present disclosure also includes those embodiments wherein the R1 group is appended to the proximal end of the alkoxylate moiety with respect to the carbonyl carbon. The present invention further includes cases where more than a single alkylene oxide is employed as alkoxylating agent, including without limitation the use of a mixture of ethylene oxide and propylene oxide to produce a random distribution of mixed alkoxy moieties. Additionally, the present invention includes block additions of alkylene oxides, such as for example reacting first a quantity of one alkylene oxide and subsequently reacting a different alkylene oxide.

From the above reaction, it is seen that a catalyst according to the present invention is capable of catalyzing the reaction between an ester and an alkylene oxide, in which the alkylene oxide, including a plurality of alkylene oxide molecules is inserted into the ester. The present catalyst is also useful for inserting alkylene oxides into oils, such as glycerine tri-ester oils, including without limitation, vegetable and plant oils.

A catalyst according to one form of the invention was made by combining the ingredients listed in Table I in the amounts specified therein (weight percents based by the total weight of the finished catalyst). The fatty acid and glycol were mixed

TABLE I

| PRIOLEAN ® 6905 oleic acid | 35% |
| POGOL ® MP-116 glycol | 35% |
| Calcium acetate | 24% |
| Sulfuric acid | 6% | together until a homogeneous mixture resulted. Then, the calcium acetate was combined with this mixture and dispersed using the Silverson mixture until homogeneous. Finally, the sulfuric acid was added slowly to the resulting dispersion, and the mixture was again mixed on the Silverson mixer until homogeneous. The final product catalyst is a viscous oil-like liquid, which may be annealed or used as-produced.

The carboxylic acid employed as a raw material for the preparation of a catalyst according to the invention may comprise any number of carbon atoms between about 8 and about 26 and may comprise a straight-chain or it may be branched. The carboxylic acid employed as a raw material for the preparation of a catalyst according to the invention may be saturated or unsaturated. According to one form of the invention, the carboxylic acid is a fatty acid having a single double bond in its molecular structure. According to another form of the invention, the carboxylic acid is a fatty acid having two double bonds in its molecular structure. According to another form of the invention, the carboxylic acid is a fatty acid having three double bonds in its molecular structure.

According to one aspect of the present invention, it is desirable to have present in catalyst as provided herein a material selected from: poly-alkoxylated alcohols having a molecular weight between about 100 and 1000, and poly-alkoxylated glycols having a molecular weight between about 100 and 1000, and polyalkylene glycols having a molecular weight between about 100 and 1000, an alkyl-capped polyalkylene glycol having molecular weight between about 100 and 1000, and including mixtures thereof. Such materials are useful as fluidizers, and in addition are believed to provide a substrate upon which an alkylene oxide may react to either initiate or propagate a polyoxyalkylene chain. When an alkyl-capped polyalkylene glycol is used, it is preferred that the "cap" portion be a $C_1$-$C_{20}$ alkyl group.

According to another embodiment, a source of zinc is added to the catalyst at any stage during the production of the catalyst, to provide zinc to be present in the finished catalyst in any amount between about 0.1% and about 5% by weight based on the total weight of catalyst produced. The source of zinc may be a powdered solid zinc compound or salt, or may be a solution containing zinc ions, or may be a slurry of a zinc compound. Zinc oxide and zinc carboxylates (such as zinc acetate) are especially preferred and are preferably present in an amount of about 2% by weight based on the total weight of the catalysts, calculated as ZnO.

Consideration must be given to the fact that although this invention has been described and disclosed in relation to certain preferred embodiments, obvious equivalent modifications and alterations thereof will become apparent to one of ordinary skill in this art after reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. This includes elements and/or chemical species which are indicated as being optional being included as essential elements in the invention, either alone or collectively with other elements and/or species being listed as optional. Accordingly, the presently disclosed invention is intended to cover all such

What is claimed is:

1. A method for forming a catalyst useful for promoting the alkoxylation of carboxylic acids, alcohols, and esters with one or more alkylene oxides, which comprises the steps of:
   a) providing a first mixture that comprises at least two alkaline earth compounds, and optionally one or more additional materials selected from the group consisting of: a carboxylic acid; a polyalkylene glycol having a molecular weight between about 100 and 1500; an $C_1$-$C_{10}$ alkyl-capped polyalkylene glycol having molecular weight between about 100 and 1500; and mixtures including any of the foregoing;
   b) combining at least one acid with said first mixture, in order to form a second mixture,
   c) homogenizing said second mixture to yield a catalyst in the form of a homogeneous paste or homogeneous liquid.

2. A method according to claim 1 wherein said two alkaline earth compounds are substantially-ionic salts.

3. A method according to claim 1 wherein said two alkaline earth compounds comprise compounds of calcium and magnesium.

4. A method according to claim 3 wherein said alkaline earth compounds comprise a mixture of compounds of calcium and magnesium, containing between about 0.1% and 1.0% by weight of magnesium, based on the total combined weight of the calcium and magnesium present.

5. A method according to claim 1 in which the alkaline earth component comprises a mixture of alkaline earth compounds, with one of the compounds being a major component and with the other compound being a minor component, wherein the ratio of the alkaline earth atoms present in the major component to number of alkaline earth atoms in the minor component is in the range of between about 9:1 to about 10,000:1.

6. A method according to claim 1 and further comprising the step of: d) annealing said catalyst by heating it to any temperature in the range of between about 120° to about 220° C. for any amount of time between about 5 minutes under any pressure in the range of between about 0.05 torr to about 100 atmospheres.

7. A method according to claim 6 which is conducted in the substantial absence of oxygen.

8. A method according to claim 1 wherein said carboxylic acid is selected from the group consisting of: capric, caprylic, caproic, octanoic, decanoic, docosanoic, dodecanoic, tetradecanoic, oleic, hexadecanoic, linoleic, and linolenic, octadecanoic.

9. A method according to claim 1 wherein said additional materials comprise a methyl ether-capped polyalkylene glycol having a molecular weight between about 100 and 1000.

10. A method according to claim 1 wherein said alkaline earth compounds are substantially ionic and comprise an anionic portion, and wherein the dissociation constant of said acid is greater than the dissociation constant of the conjugate acid of said anionic portion.

11. A method according to claim 1 wherein said acid is sulfuric acid which contains between about 10% and 99.9% by weight of $H_2SO_4$.

12. A method according to claim 1 wherein said acid is selected from the group consisting of: an alkylbenzene sulfonic acid, an alkylbenzene sulfonate salt, para-toluene sulfonic acid, a para-toluene sulfonate salt, naphthalene sulfonates, naphthalene sulfonic acids, sulfosuccinamates, sulfosuccinates, and sour esters of ether sulfates.

13. A method according to claim 1 wherein one of said compounds of calcium is selected from the group consisting of: calcium acetate and calcium hydroxide, and wherein said carboxylic acid is an unsaturated carboxylic acid.

14. A method according to claim 13 wherein said carboxylic acid comprises oleic acid.

15. A method according to claim 1 wherein one of said alkaline earth compounds is an ionic calcium compound whose anionic portion comprises the anion of a carboxylic acid.

16. A method according to claim 1 wherein one of said alkaline earth compounds comprises an overbased sulfonate.

17. A method for alkoxylating an organic material selected from the group consisting of: alcohols and esters, which comprises treating said organic material with an alkylene oxide selected from the group consisting of: ethylene oxide, propylene oxide, and butylene oxide in the presence of a catalyst produced according to a process described in claim 1.

18. A method according to claim 17 in which said catalyst exists in the form of an opaque substance at room temperature.

19. An alkoxylation process useful for converting organic carboxy compounds into molecules having surfactant properties, which process proceeds according to the scheme:

$$R_1-CH-CH_2 \ + \ R_2-\overset{O}{\overset{\|}{C}}-O-R_3 \ \dashrightarrow$$
$$\overset{O}{\underset{}{}}$$

$$R_2-\overset{O}{\overset{\|}{C}}-O-(CH_2CHO)_n-R_3$$
$$\underset{R_1}{|}$$

in which $R_1$ is independently selected from the group consisting of: hydrogen and any $C_1$-$C_4$ alkyl group; $R_2$ is independently any $C_6$ to $C_{24}$ hydrocarbyl group, and $R_3$ is independently hydrogen or any $C_1$-$C_6$ hydrocarbyl group, n is any integer between about 1 and 30, and wherein said process is conducted in the presence of a catalyst as described in claim 1.

20. A method for enhancing the rate of reaction of a process according to claim 19 which comprises the step of adding a ternary mixture comprising a carboxylic acid, a $C_1$-$C_8$ alcohol, and a polyalkylene glycol having molecular weight between about 100 and about 1000 to the reactants at any stage prior to completion of the reaction, wherein the amount of said ternary mixture added is between about 0.1% and about 10% by weight based on the total weight of the reactant organic carboxy compound.

21. A method for enhancing the rate of reaction of a process according to claim 19 which comprises the step of adding a ternary mixture comprising a carboxylic acid, a $C_1$-$C_8$ alcohol, and a polyalkylene glycol having molecular weight between about 100 and about 1000 to the reactants at any stage prior to completion of the reaction, wherein the amount of said ternary mixture added is between about 0.1% and about 10% by weight based on the total weight of the reactant organic carboxy compound.

22. A method for enhancing the rate of reaction of a process according to claim 19 which comprises the step of adding a ternary mixture comprising a carboxylic acid, a $C_1$-$C_8$ alcohol, and a $C_1$ to $C_{10}$ alkyl-capped polyalkylene glycol having molecular weight between about 100 and about 1000 to the reactants at any stage prior to completion of the reaction, wherein the amount of said ternary mixture added is between about 0.1% and about 10% by weight based on the total weight of the reactant organic carboxy compound.

23. A method according to claim 19 wherein said catalyst comprises zinc, in any amount between 0.1% and 5% by weight based on the total weight of said catalyst.

24. An alkoxylation process useful for converting glyceryl triesters into molecules having surfactant properties, which process comprises adding a $C_1$-$C_4$ alkylene oxide to a glyceryl triester in the presence of a catalyst as described in claim 1.

25. An alkoxylation catalyst comprising a product obtained by mixing at least:
   an alkaline earth compound;
   a carboxylic acid having between about 2 and 25 carbon atoms;
   a polyalkylene glycol having a molecular weight between about 100 and 1500 or an $C_1$-$C_{10}$ alkyl-capped polyalkylene glycol having molecular weight between about 100 and 1500 or a mixure thereof; and
   a strong acid.

26. The alkoxylation catalyst of claim 25 wherein the alkaline earth compound is an alkaline earth metal salt.

27. The alkoxylation catalyst of claim 26 wherein the alkaline earth compound is a calcium salt.

28. The alkoxylation catalyst of claim 27 wherein the calcium salt is calcium acetate.

29. The alkoxylation catalyst of claim 25 wherein the carboxylic acid is a saturated fatty acid.

30. The alkoxylation catalyst of claim 25 wherein the carboxylic acid is a fatty acid having from one to three double bonds.

31. The alkoxylation catalyst of claim 30 wherein the carboxylic acid is oleic acid.

32. The alkoxylation catalyst of claim 25 wherein the polyalkylene glycol is polyethylene glycol.

33. The alkoxylation catalyst of claim 25 wherein the $C_1$-$C_{10}$ alkyl-capped polyalkylene glycol is methoxy polyethylene glycol.

34. The alkoxylation catalyst of claim 25 wherein the strong acid is sulfuric acid.

35. The alkoxylation catalyst of claim 25 wherein the alkaline earth compound is calcium acetate, the carboxylic acid is oleic acid, the polyalkylene glycol is polyethylene glycol, and the strong acid is sulfuric acid.

36. The alkoxylation catalyst of claim 25 wherein the alkaline earth compound is calcium acetate, the carboxylic acid is oleic acid, the $C_1$-$C_{10}$ alkyl-capped polyalkylene glycol is methoxy polyethylene glycol, and the strong acid is sulfuric acid.

37. The alkoxylation catalyst of claim 25 wherein the alkaline earth compound is about 24 weight percent of the catalyst, the carboxylic acid is about 35 weight percent of the catalyst, the $C_1$-$C_{10}$ alkyl-capped polyalkylene glycol is about 35 weight percent of the catalyst, and the strong acid is about 6 weight percent of the catalyst.

* * * * *